(12) United States Patent
Yoon et al.

(10) Patent No.: US 10,828,331 B2
(45) Date of Patent: Nov. 10, 2020

(54) CELLULAR COMPOSITIONS USED TO RESTORE STEM CELL OR PROGENITOR CELL FUNCTION AND METHODS RELATED THERETO

(71) Applicant: Emory University, Atlanta, GA (US)

(72) Inventors: Young-Sup Yoon, Atlanta, GA (US); Ji Woong Han, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/440,555

(22) Filed: Feb. 23, 2017

(65) Prior Publication Data

US 2017/0157178 A1 Jun. 8, 2017

Related U.S. Application Data

(62) Division of application No. 14/438,894, filed as application No. PCT/US2013/068505 on Nov. 5, 2013, now abandoned.

(Continued)

(51) Int. Cl.
*A61K 35/28* (2015.01)
*C07D 239/95* (2006.01)
(Continued)

(52) U.S. Cl.
CPC ............ *A61K 35/28* (2013.01); *A61K 35/44* (2013.01); *C07D 239/95* (2013.01);
(Continued)

(58) Field of Classification Search
CPC .. C07D 401/14; C07D 401/12; C07D 239/95; C12N 5/0663; C12N 2501/065; C12N 2501/40; A61K 35/28; A61K 35/44
See application file for complete search history.

(56) References Cited

U.S. PATENT DOCUMENTS

| 3,956,495 A | 5/1976 | Lacefield |
| 2004/0248890 A1 | 12/2004 | Gonzalez |
| 2007/0265286 A1 | 11/2007 | Thomas |

FOREIGN PATENT DOCUMENTS

WO 2004030672 4/2004

OTHER PUBLICATIONS

Feng et al. Suberoylanilide hydroxamic acid promotes cardiomyocyte differentiation of rat mesenchymal stem cells. Experimental Cell Research (2009), v315, p. 3044-3051. (Year: 2009).*

(Continued)

*Primary Examiner* — Sean C. Barron
(74) *Attorney, Agent, or Firm* — Emory Patent Group

(57) ABSTRACT

This disclosure relates to compounds, compositions and methods of epigenetically transforming cells. In certain embodiments, the disclosure relates to methods of generating epigenetically altered cells comprising mixing isolated cells with compositions disclosed herein under conditions such that epigenetically altered cells are formed. In certain embodiments, methods of treating or preventing vascular or diabetic diseases or conditions are contemplated. In certain embodiments, epigenetically reprogramming adult bone marrow-derived stem or progenitor cells including mesenchymal stem cells (MSCs) or endothelial progenitor cells (EPCs) for autologous treatments are contemplated.

5 Claims, 8 Drawing Sheets

Related U.S. Application Data

(60) Provisional application No. 61/723,846, filed on Nov. 8, 2012.

(51) Int. Cl.
*C07D 401/12* (2006.01)
*C07D 401/14* (2006.01)
*C12N 5/0775* (2010.01)
*A61K 35/44* (2015.01)

(52) U.S. Cl.
CPC ......... *C07D 401/12* (2013.01); *C07D 401/14* (2013.01); *C12N 5/0663* (2013.01); *C12N 2501/065* (2013.01); *C12N 2501/40* (2013.01)

(56) References Cited

OTHER PUBLICATIONS

Kuo et al. Bone Marrow-Derived Mesenchymal Stem Cells Enhanced Diabetic Wound Healing through Recruitment of Tissue Regeneration in a Rat Model of Streptozotocin-Induced Diabetes. Plast Reconstr Surg (Oct. 2011), v128(4), p. 872-880. (Year: 2011).*
Glass et al. Stem cells in the diabetic infarcted heart. Heart Fail Rev (2010), v15(6), p. 581-588. (Year: 2010).*
Voltarelli et al. Stem cell transplantation for type 1 diabetes mellitus. Diabetology and Metabolic Syndrome (2009), v1(4), 4 pages. (Year: 2009).*
AJF King. The use of animal models in diabetes research. British Journal of Pharmacology (2012), v166, p. 877-894. (Year: 2012).*
Shim et al. Ex vivo differentiation of human adult bone marrow stem cells into cardiomyocyte-like cells. BBRC (2004), 324, 481-488. (Year: 2004).*
Benning et al. Quinazoline-derived alpha 1-Adrenoceptor Antagonists Induce Prostate Cancer Cell Apoptosis Via an alph 1-Adrenoceptor-independent Action, Cancer Research 62, 597-602, 2002.
Chang et al. Adding a Lysine Mimic in the Design of Potent Inhibitors of Histone Lysine Methyltransferases, J Mol Biol. 2010, 400(1): 1-7.
Condorelli et al. Cardiomyocytes induce endothelial cells to trans-differentiate into cardiac muscle: Implications for myocardium regeneration, Proc Natl Acad Sci U S A. 2001, 98(19):10733-8.
Feng et al. Suberoylanilide hydroxamic acid promotes cardiomyocyte differentiation of rat mesenchymal stem cells, Exp Cell Res. 2009, 315(17):3044-51.
Gibson et al. Epidermal Growth Factor Receptor Tyrosine Kinase: Structure-Activity Relationships and Antitumour Activity of Novel Quinazolines, Bioorganic & Medicinal Chemistry Letters, vol. 7, No. 21, pp. 2723-2728, 1997.
Glass et al. Stem cells in the diabetic infarcted heart, Heart Fail Rev (2010) 15:581-588.
Han et al. Cell Therapy for Diabetic Neuropathy Using Adult Stem or Progenitor Cells, Diabetes Metab J 2013, 37:91-105.
Han et al. Bone Marrow-Derived Mesenchymal Stem Cells Improve Diabetic Neuropathy by Direct Modulation of Both Angiogenesis and Myelination in Peripheral Nerves, Cell Transplant. 2016, 25(2): 313-326.
Kim et al. Diabetic Mesenchymal Stem Cells Are Ineffective for Improving Limb Ischemia Due to Their Impaired Angiogenic Capability, Cell Transplant. 2015, 24(8): 1571-1584.
Kuo et al. Bone Marrow-Derived Mesenchymal Stem Cells Enhanced Diabetic Wound Healing through Recruitment of Tissue Regeneration in a Rat Model of Streptozotocin-Induced Diabetes. Plast Reconstr Surg (2011), v128(4), p. 872-880.
Li et al. Paracrine factors released by GATA-4 overexpressed mesenchymal stem cells increase angiogenesis and cell survival, Am J Physiol Heart Circ Physiol 299: H1772-H1781, 2010.
Liu et al. Discovery of a 2,4-Diamino-7-aminoalkoxy-quinazoline as a Potent and Selective Inhibitor of Histone Lysine Methyltransferase G9a, J Med Chem. 2009, 52(24): 7950-7953.
Lynch et al. Activating Mutations in the Epidermal Growth Factor Receptor Underlying Responsiveness of Non-Small-Cell Lung Cancer to Gefitinib, N Engl J Med 2004, 350:2129-39.
Mezentseva et al. The Histone Methyltransferase Inhibitor BIX01294 Enhances the Cardiac Potential of Bone Marrow Cells, Stem Cells Dev. 2013, 22(4):654-67.
Orlic et al. Bone marrow cells regenerate infarcted myocardium, Nature. 2001, 410(6829):701-5.
Oscher et al. Obesity in Elderly Subjects, Diabetes Care. 2009, 32(Suppl 2): S398-S402.
Shi et al. A Combined Chemical and Genetic Approach for the Generation of Induced Pluripotent Stem Cells, Cell Stem Cell. 2008, 2(6):525-8.
Upadhyay et al. An analog of Bix-01294 selectively inhibits a family of histone H3 lysine 9 Jumonji demethylases, J Mol Biol. 2012, 416(3): 319-327.
Voltarelli et al. Stem cell transplantation for type I diabetes mellitus, Diabetology & Metabolic Syndrome 2009, 1:4.
Zhu et al. Reprogramming of Human Primary Somatic Cells by OCT4 and Chemical Compounds, Cell Stem Cell. 2010, 7(6):651-5.
Cramer et al. Persistent High Glucose Concentrations Alter the Regenerative Potential of Mesenchymal Stem Cells, Stem Cells and Development vol. 19, No. 12, 2010.
Shin et al., Impaired therapeutic capacity of autologous stem cells in a model of type 2 diabetes, Stem cells translational medicine, 2012, 1, 125-135.
Yan et al., Type 2 diabetes restricts multipotency of mesenchymal stem cells and impairs their capacity to augment post-ischemic neovascularization in db/db mice, J Am Heart Assoc, 2012, 1, e002238.

* cited by examiner

| Genes | Fold (Normal vs DM) | Genes | Fold (Normal vs DM) |
|---|---|---|---|
| Adr 2b | 2.6 | Nudt6 | 5.60 |
| Akt | 13.1 | PDGFb | 4.60 |
| CXCl 10 | 1.7 | Prokinecin 2 | 4.3 |
| FGF 2 | 2.1 | PTEN | 2.4 |
| FGF 6 | 1.6 | PTGS-1 | 2.0 |
| HGF | 9.4 | PTGS-2 | 2.0 |
| HIF 1a | 3.3 | Sphk 1 | 6.4 |
| IFNγ | 1.4 | TNF | 5.0 |
| IL 6 | 3.4 | TNFR | 2.0 |
| KDR | 4.6 | VEGF-A | 3.4 |
| Laminin, A5 | 1.7 | VEGF-B | 7.8 |
| MAP kinase 14 | 6.8 | VEGF-C | 5.7 |
| MMP 19 | 1.9 | Wasf2 | 4.7 |
| Notch 4 | 2.3 | NPR B | 1.5 |
| Nrp-1 | 7.0 | | |

FIG. 12

CELLULAR COMPOSITIONS USED TO RESTORE STEM CELL OR PROGENITOR CELL FUNCTION AND METHODS RELATED THERETO

CROSS REFERENCE TO RELATED APPLICATIONS

This application is a division of U.S. application Ser. No. 14/438,894 filed Apr. 28, 2015, which is the National Stage of International Application No. PCT/US2013/068505 filed Nov. 5, 2013, which claims the benefit of U.S. Provisional Application No. 61/723,846 filed Nov. 8, 2012. The entirety of each of these applications is hereby incorporated by reference for all purposes.

STATEMENT REGARDING FEDERALLY FUNDED RESEARCH

This invention was made with government support under Grant 1DP3DK04346-01 awarded by the National Institutes of Health. The government has certain rights in the invention.

BACKGROUND

Obesity and old age are risk factors for cardiovascular disease, diabetes, and chronic kidney disease. See Osher & Stern, Diabetes Care, 2009, 32(2):5398-5402. Often they occur together indicating a mechanistic relationships. The migration of circulating bone-marrow-derived stem cells to the site of damaged tissue is typically not sufficient to restore the myocardium after a heart attack. Typical cardiovascular compounds such as beta-blockers, diuretics, and angiotensin-converting enzyme (ACE) inhibitors do not restore function to damaged tissue. Thus, there is a need to identify improved methods of treating cardiovascular disease.

One strategy to treat cardiovascular disease is by restoring damaged tissue through regeneration. Embryonic and adult-derived stem cells for have been investigated. Orlic et al., Nature, 2001, 410:701-705, report that bone marrow cells regenerate infarcted myocardium. See also Condorelli et al. Proc Natl Acad Sci USA., 2001, 98:10733-10738. Wu et al., Stem Cells, 2007, 25:2648-2659, report that mesenchymal stem cells enhance wound healing through differentiation and angiogenesis.

Shi et al., Cell Stem Cell, 2008, 2(6):525-8, report that BIX01294 and BayK8644, in combination with two factors (Oct4 and Klf4), enhanced the reprogramming efficiency of mouse neural progenitors and mouse embryonic fibroblasts. Upadyay et al., J Mol Biol, 2012, 416(3):319-27, report that an analog of BIX-01294 selectively inhibits a family of histone H3 lysine 9 Jumonji demethylases.

References cited herein are not an admission of prior art.

SUMMARY

This disclosure relates to compounds, compositions and methods of epigenetically transforming cells. In certain embodiments, the disclosure relates to methods of generating epigenetically altered cells comprising mixing isolated cells with compositions disclosed herein under conditions such that epigenetically altered cells are formed. In certain embodiments, methods of treating or preventing vascular or diabetic diseases or conditions are contemplated.

In certain embodiments, the disclosure contemplates methods of epigenetically modifying stem or progenitor cells comprising mixing the stem or progenitor cells and compositions comprising compounds disclosed wherein such as a quinazoline compound, 5-aza-2'-deoxycytidine, or/and N-Phthalyl-L-tryptophan (RG108), under conditions such that cells with enhanced angiogenic gene expression are produced. In certain embodiments, the conditions are such that reduced DNA methylation in the promoters of angiogenic genes occurs. In certain embodiments, the angiogenic genes are one or more or all of the genes selected from Akt1, Hgf, Mapk14, Sphk1, Vegfc, Nudt6, Kdr, Vegfa, and Pten.

In certain embodiments, the stem or progenitor cells are mesenchymal stem cells (MSCs) or endothelial progenitor cells (EPCs), cardiac stem cells, myoblasts, adult bone marrow-derived cells, umbilical cord blood cells, fibroblasts, or peripheral blood $CD34^+$ cells. In certain embodiments, the endothelial progenitor cells are bone marrow derived. In certain embodiments, the cells are obtained from a subject diagnosed with diabetes and/or cardiovascular disease.

In certain embodiments, the composition comprise mixtures of compounds disclosed herein. I certain embodiments, the composition comprises a quinazoline compound optionally in combination with DNA methyltransferase inhibitor, a histone deacetylase (HDAC) inhibitor, DNA methylation inhibitor, a Rho-associated kinase (ROCK) inhibitor, Wnt inhibitor, GSK-3beta inhibitor, and/or a dihydropyridine. In certain embodiments, the DNA methyltransferase inhibitor is N-phthalyl-L-tryptophan (RG 108). In certain embodiments, the DNA methylation inhibitor is 5-azacitidine or decitabine. In certain embodiments, the HDAC inhibitor is vorinostat-suberoylanilide hydroxamic acid (SAHA), trichostatin A (TSA), or valproic acid (VPA). In certain embodiments, the ROCK inhibitor is 4-(1-aminoethyl)-N-(pyridin-4-yl)cyclohexanecarboxamide (Y-27632) or salt thereof. In certain embodiments, the dihydropyridine is 1,4-dihydro-2,6-dimethyl-5-nitro-4-[2-(trifluoromethyl)phenyl]-3-pyridinecarboxylic acid, methyl ester (BayK8644), ester, derivative, or salt thereof. In certain embodiments, the GSK-3beta inhibitor is 6-[[2-[[4-(2,4-dichlorophenyl)-5-(5-methyl-1H-imidazol-2-yl)-2 pyrimidinyl]amino]ethyl]amino]-3-pyridinecarbonitrile (CHIR99201) or salt thereof. In certain embodiments, the quinazoline compound has formula I, formula IA, or formula II.

In certain embodiments, the disclosure contemplates methods of treating or preventing vascular disease or condition comprising: mixing progenitor cells from a subject and a composition as provided herein under conditions such that epigenetically modified cells with enhanced angiogenic gene expression are produced; and administering an effective amount of a composition comprising the epigenetically modified cells or cells cultured therefrom to a subject in need thereof. In certain embodiments, the progenitor cells are bone marrow derived cells, endothelial progenitor cells, or mesenchymal stem cells. In certain embodiments, the progenitor cells were obtained from the subject receiving the administered composition. In certain embodiments, the vascular disease or condition is peripheral vascular disease, myocardial ischemia, cardiovascular disease, heart failure, or stroke.

In certain embodiments, the disclosure contemplates methods of treating or preventing a diabetic disease or conditions comprising: mixing progenitor cells from a subject and a composition as provided herein under conditions such that epigenetically modified cells with enhanced angiogenic gene expression are produced; and administering an effective amount of a composition comprising the epigenetically modified cells or cells cultured therefrom to a subject in need thereof. In certain embodiments, the progenitor cells are bone marrow derived cells, endothelial progenitor cells, or mesenchymal stem cells. In certain embodiments, the progenitor cells were obtained from the subject receiving the administered composition. In certain embodiments, the diabetic disease or condition is diabetic wounds or diabetic neuropathy.

In certain embodiments, the epigenetically modified cells may be cultured, expanded, or replicated in order to provide enhanced concentrations upon administration/transplantation and the modified cells may be autologous (i.e., derived from the person on whom they are used) or allogeneic (i.e., originating from another person) in origin. In certain embodiments, methods include those subjects that are co-morbid with a vascular disease or condition and a diabetic disease or condition.

In certain embodiments, the disclosure contemplates intravenous injection and direct infusion into the coronary arteries. In certain embodiments, the methods can be used in subject whose blood flow has been restored to their hearts after a heart attack. In certain embodiments, the compositions are injected directly into the ventricular wall of the subject, i.e., endo-myocardial injection or into the peritoneal cavity, and may be carried out either via a catheter or during open-heart surgery.

In certain embodiments, the disclosure contemplates methods of treating diseases or conditions disclosed herein comprising administering effective amounts of pharmaceutical compositions disclosed herein comprising a compound or mixture of compounds to a subject in need thereof.

In certain embodiments, treating or preventing kidney disease or wound healing by methods disclosed herein are contemplated.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

BRIEF DESCRIPTION OF THE DRAWINGS

FIG. 12 shows microarray results of mRNA expression of angiogenic genes.

DETAILED DESCRIPTION

Figure 1:
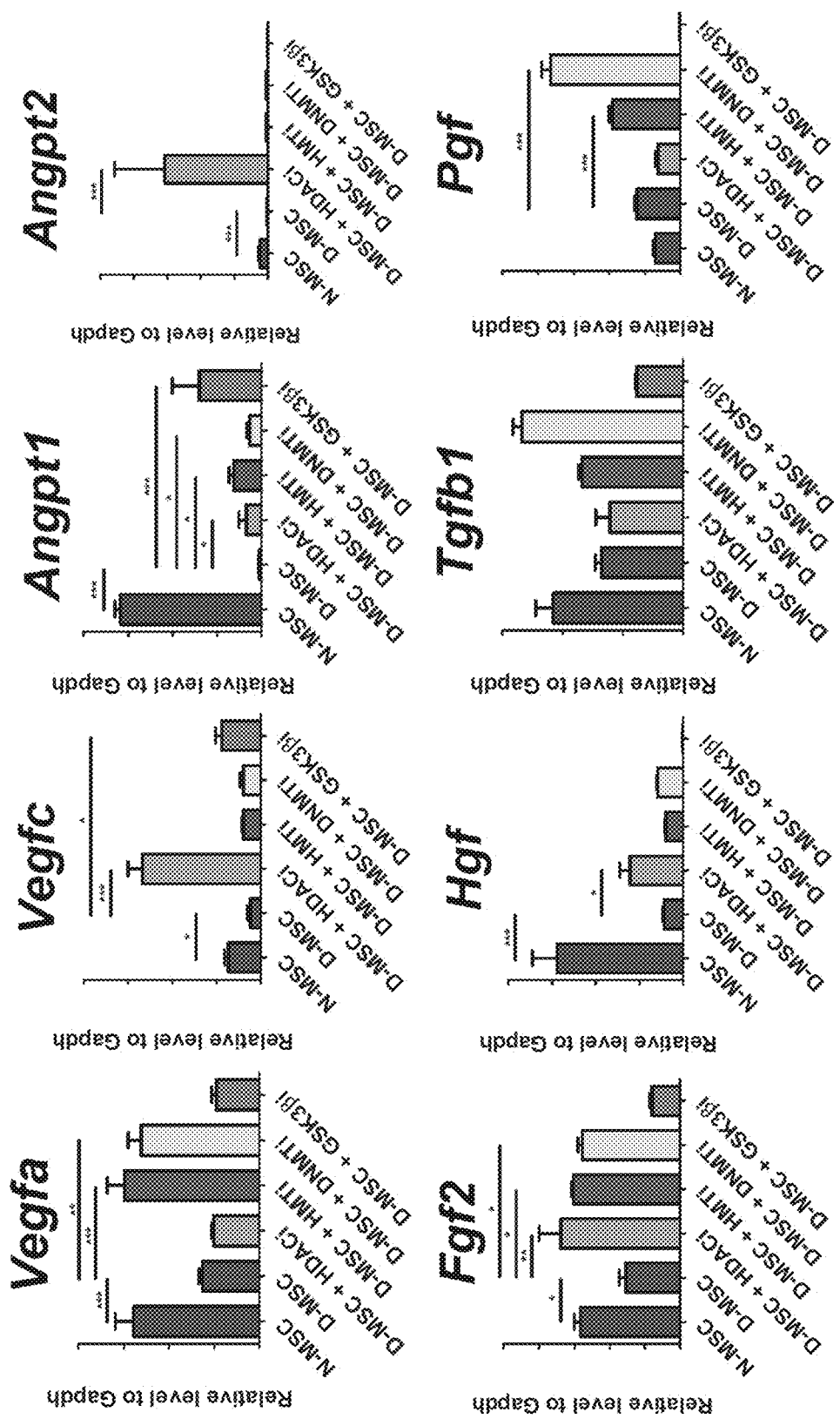
FIG. 1 shows data suggesting the restoration of gene expression of angiogenic genes in diabetic MSCs with compounds.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term "induced pluripotent stem cells" refers to cells induced to a state that can differentiate into at least one cell of the endoderm, mesoderm and ectoderm. Such characteristics include the expression of certain genes and proteins, chromatic methylation patterns, doubling time, embryoid body formation, teratoma formation, and differentiability. Induced pluripotent stem cells typically express alkaline phosphatase, Oct 4, Sox2, Nanog, and other pluripotency-promoting factors. It is not intended that the cells be entirely identical to embryonic cells. Induced pluripotent stem cells may not necessarily be capable of differentiating into any type of cell. SSEA-1 is a mouse ESC/iPSC specific marker; SSEA-3 and -4 are not expressed in mouse ESC/iPSC. However, human ESC/iPSC express SSEA-3 and SSEA-4, not SSEA-1. SSEA-1 is mouse iPSC specific. SSEA-3, SSEA-4 is human iPSC specific. TRA-1-60 and TRA-1-8 are usually used to identify human PSC.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the term "combination with" when used to describe administration with an additional treatment means that the agent may be administered prior to, together with, or after the additional treatment, or a combination thereof.

Epigenetic Regulation and Methods of Restoration of Diabetic Cell Function

Gene expression is affected by chromatin. Chromatin is the complex of DNA and the histone proteins. Chromatin remodeling occurs through post translational modification of the histone proteins. Chromatic remodeling may also occur with the addition of methyl groups to the DNA. Cytosines are often converted to 5-methylcytosine in CG sequences of DNA, often referred to as methylated "CpGs." 5-Methylcytosine, like cytosine, pairs with guanine. Highly methylated DNA tends to be less transcriptionally active. Histone acetylation, methylation, ubiquitylation, and phosphorylation modifications typically occur at the N-termini of histones. For example, acetylation of the K14 and K9 lysines of the tail of histone H3 by histone acetyltransferase enzymes (HATs) has typically been correlated with transcriptional competence. Methylation of lysine 9 of histone H3 has typically been associated with constitutively transcriptionally silent chromatin.

Adult bone marrow-derived stem or progenitor cells including mesenchymal stem cells (MSCs) or endothelial progenitor cells (EPCs) are very useful for repairing cardiovascular disease; however, autologous cells derived from diabetic patients are not as effective as those from non-diabetic or healthy volunteers. As many cardiovascular disease patients who are candidates for cell therapy have diabetes as co-morbid disease which reduce the therapeutic effects of stem or progenitor cells derived from patient own bodies. Studied disclosed herein indicate that EPCs and MSCs have significant epigenetic changes in the promoter regions of angiogenic factors and these defects reduce the functionality of the cells. Certain disclosed herein are epigenetic modulators can rescue gene expression of these progenitor and stem cells and thus restore their tissue repairing and angiogenic capacities. The candidate diseases that are applied by this new cell therapy include peripheral vascular disease, myocardial ischemia, heart failure, diabetic wounds, diabetic neuropathy, and stroke.

Reversing epigenetic alterations with small molecules can restore gene expression and cell biologic function of diabetic bone marrow-derived cells (D-BMCs). Studies herein indicate that diabetic EPCs (D-EPCs) have high methylation in the promoter regions of angiogenic genes and compounds disclosed herein can reverse these changes, increase gene expression and improve cellular function. In certain embodiments, the disclosure contemplates composition comprising compounds or combinations of: DNA methyltransferase inhibitors (e.g., 5-Aza-2'-Deoxycytidine, 5-Aza or RG1 08), histone deacetylase (HDAC) inhibitors (e.g., valproic acid, VPA), and histone methyltransferase (HMT) inhibitors (e.g., compounds of formula I for G9a and GLP HMTs).

Quinazoline Compounds

In certain embodiments, the disclosure contemplates the use of quinazoline compounds disclosed herein to generate epigenetically altered cells. Although it is not intended that certain embodiments of the disclosure be limited by any particular mechanism, it is believed that the compounds typically have the ability to inhibit the function of methyltransferases such as G9a methyltransferase.

In certain embodiments, contemplated quinazoline compounds have Formula I:

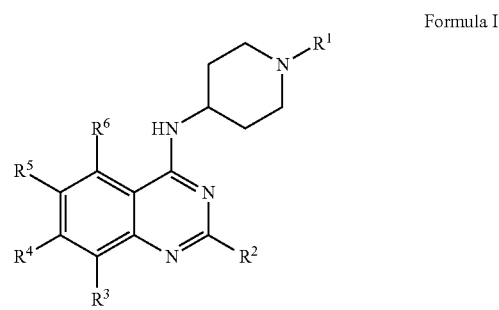

Formula I or salts thereof wherein, $R^1$, $R^2$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each $R^1$, $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^7$ is optionally substituted with one or more, the same or different, $R^8$; and $R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is alkoxy optionally substituted with one or more, the same or different, $R^7$.

In certain embodiments, $R^2$ is alkylamino optionally substituted with one or more, the same or different, $R^7$.

In certain embodiments, $R^2$ is a heterocyclyl optionally substituted with one or more, the same or different, $R^7$.

In certain embodiments, $R^1$ is alkyl or benzyl optionally substituted with one or more, the same or different, $R^7$.

In certain embodiments, contemplated quinazoline compounds have Formula IA:

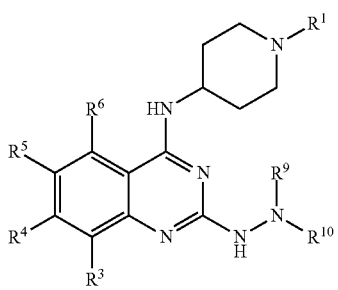

Formula IA or salts thereof wherein, $R^1$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, aryl sulfonyl, carbocyclyl, aryl, or heterocyclyl, wherein each $R^1$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, arylsulfonyl, carbocyclyl, aryl, or heterocyclyl, wherein $R^7$ is optionally substituted with one or more, the same or different, $R^8$;

$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethyl sulfamoyl, N,N-diethylsulfamoyl, N-methyl-N-ethylsulfamoyl, carbocyclyl, aryl, or heterocyclyl;

$R^9$ and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, aryl sulfonyl, carbocyclyl, aryl, or heterocyclyl, wherein each $R^9$ and $R^{10}$ are optionally substituted with one or more, the same or different, $R^{11}$;

or $R^9$ and $R^{10}$ come together to form a heterocyclyl optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methyl sulfamoyl, N-ethyl sulfamoyl, N,N-dimethyl sulfamoyl, N,N-diethylsulfamoyl, N-methyl-N-ethylsulfamoyl, carbocyclyl, aryl, or heterocyclyl.

In certain embodiments, contemplated quinazoline compounds are selected from:

N-(1-benzylpiperidin-4-yl)-2-(4-methylpiperazin-1-yl)quinazolin-4-amine,

N-(1-benzylpiperidin-4-yl)-2-(4-methyl-1,4-diazepan-1-yl)quinazolin-4-amine,

N-(1-benzylpiperidin-4-yl)-6,7-dimethoxy-2-(4-methyl-1,4-diazepan-1-yl)quinazolin-4-amine, N-(1-benzylpiperidin-4-yl)-6,7-dimethoxy-2-(4-methylpiperazin-1-yl)quinazolin-4-amine, N-(1-benzylpiperidin-4-yl)-6,7-dimethoxy-2-morpholinoquinazolin-4-amine, N-(1-benzylpiperidin-4-yl)-2-morpholinoquinazolin-4-amine, N-(1-benzylpiperidin-4-yl)-2-thiomorpholinoquinazolin-4-amine, N-(1-benzylpiperidin-4-yl)-2-(piperidin-1-yl)quinazolin-4-amine, 2-(azepan-1-yl)-N-(1-benzylpiperidin-4-yl)quinazolin-4-amine, N-(1-benzylpiperidin-4-yl)-2-(4-methylpiperidin-1-yl)quinazolin-4-amine, $N^4$-(1-benzylpiperidin-4-yl)-$N^2$-(piperidin-1-yl)quinazoline-2,4-diamine, N-(1-benzylpiperidin-4-yl)-2-(pyrrolidin-1-yl)quinazolin-4-amine, N-(1-benzylpiperidin-4-yl)-2-(4-(pyridin-2-yl)piperazin-1-yl)quinazolin-4-amine, (4-(4-((1-benzylpiperidin-4-yl)amino)quinazolin-2-yl)piperazin-1-yl)(phenyl)methanone, $N^4$-(1-benzylpiperidin-4-yl)-$N^2$-(3-(dimethylamino)propyl)quinazoline-2,4-diamine, 2-((4-((1-benzylpiperidin-4-yl)amino)quinazolin-2-yl)amino)ethanol, $N^4$-(1-benzylpiperidin-4-yl)-$N^2$-(4-methylpiperazin-1-yl)quinazoline-2,4-diamine, $N^4$-(1-benzylpiperidin-4-yl)-$N^2$-morpholinoquinazoline-2,4-diamine, N-(1-benzylpiperidin-4-yl)-2-(2-methylpiperidin-1-yl)quinazolin-4-amine, 7-((5-aminopentyl)oxy)-$N^4$-(1-benzylpiperidin-4-yl)-$N^2$-(3-(dimethylamino)propyl)-6-methoxyquinazoline-2,4-diamine, N-(1-benzylpiperidin-4-yl)-2-(4-phenylpiperazin-1-yl)quinazolin-4-amine, and 7-((5-aminopentyl)oxy)-$N^4$-(1-(5-aminopentyl)piperidin-4-yl)-$N^2$-(3-(dimethylamino)propyl)-6-methoxyquinazoline-2,4-diamine or salts thereof.

In certain embodiments, contemplated quinazoline compounds have Formula II:

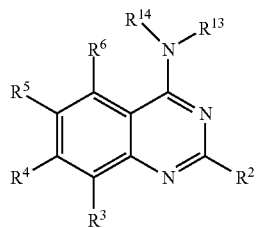

Formula II or salts thereof wherein, $R^2$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, arylsulfonyl, carbocyclyl, aryl, or heterocyclyl, wherein $R^7$ is optionally substituted with one or more, the same or different, $R^8$;

$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$ and $R^{14}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{13}$ and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{13}$ and $R^{14}$ are hydrogen or alkyl optionally substituted with one or more, the same or different, $R^{15}$.

In certain embodiments, $R^4$ is alkoxy optionally substituted with one or more, the same or different, $R^7$.

In certain embodiments, $R^2$ is alkylamino optionally substituted with one or more, the same or different, $R^7$.

In certain embodiments, $R^2$ is a alkyl or heterocyclyl optionally substituted with one or more, the same or different, $R^7$.

In certain embodiments, contemplated quinazoline compounds are selected from:

7-((5-aminopentyl)oxy)-$N^2$-(3-(dimethylamino)propyl)-6-methoxy-$N^4$,$N^4$-dimethylquinazoline-2,4-diamine and 7-((5-aminopentyl)oxy)-6-methoxy-$N^2$,$N^2$,$N^4$,$N^4$-tetramethylquinazoline-2,4-diamine or salts thereof.

EXAMPLES

Restore of Epigenetic Silencing of Angiogenic Genes in Diabetic MSCs by Compound Epigenetic Regulators To reprogram diabetic MSCs with epigenetic compounds, cultured D-MSCs were treated with HDAC inhibitor: Vorinostat or suberoylanilide hydroxamic acid (SAHA); DNA methyltransferase inhibitor: Decitabine (trade name Dacogen), or 5-aza-2'-deoxycytidine (5-aza); multiple histone 3 lysine 9 (H3K9) methyltransferases G9a and GLP inhibitor: BIX-01294; and GSK3β inhibitor: CHIR99021 for 7 more days. N-MSCs and D-MSCs were cultured by a standard MSC culture method. The cultured MSCs are typically reseeded at day 4 and cultured for another 4 days. To examine the expression levels of angiogenic genes, we isolated RNAs from N-, D-, or epigenetic compound treated reprogrammed D-MSCs (RD-MSCs), and performed real-time RT-PCR with specific primers of angiogenic genes. The expression of major angiogenic genes of RD-MSCs were significantly higher than D-MSCs up to N-MSCs or more (FIG. 1) although different type of inhibitors showed different pattern of gene expression. This result indicated that defective expression of angiogenic gene in D-MSCs could be restored by epigenetic modification by treatment of known epigenetic compounds. Among inhibitors, HDAC inhibitor showed significant increased pattern in most of genes, therefore, HDAC inhibitor, SAHA, was selected for following experiments.

Figure 2:
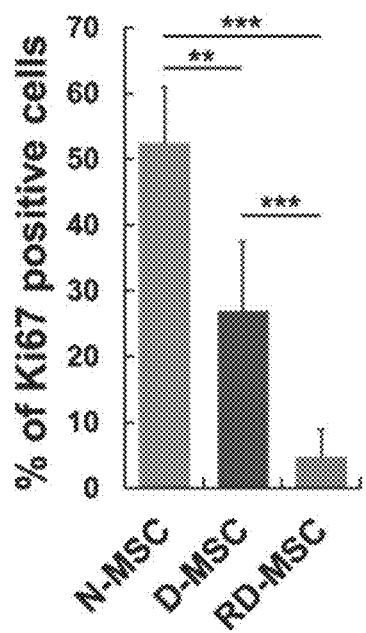
FIG. 2 shows data on impaired proliferation of D-MSCs.
Figure 3:
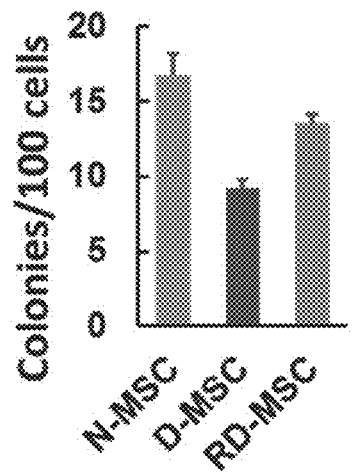
FIG. 3 shows data on the restoration of impaired proliferation of D-MSCs with compounds.

Restore of Impaired Cell Proliferation and Survival of Diabetic MSCs with Compound To determine whether diabetes can affect the cell proliferation capacity of MSCs, immunocytochemistry was performed for Ki67, an effective marker for mitosis. The percentage of Ki67-positive cells was 53% lower in D-MSCs compared to N-MSCs (FIG. 2). To determine whether this was due to the slow proliferation of D-MSCs compared to N-MSCs, a colony forming unit assay was performed, which determines actively proliferating cell portions. The number of colony forming units (colonies/100 cells) was 45% smaller in D-MSCs compared to N-MSCs, while RD-MSCs restored the number of colony forming up to 80% of N-MSCs (FIG. 3), suggesting that the proportion of actively proliferating cells is smaller in D-MSCs than N-MSCs which could be restored by the treatment of compounds.

Figure 4:
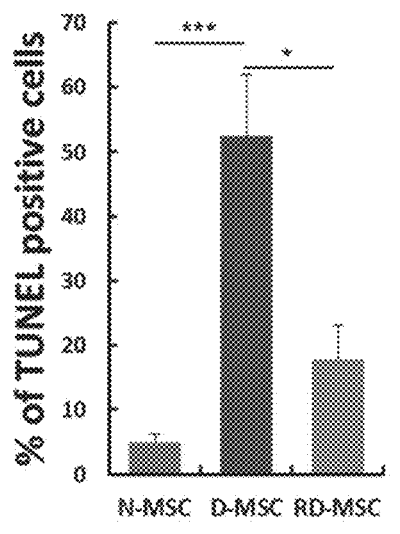
FIG. 4 shows data on the restoration of impaired cell survival of diabetic MSCs with compounds.

Furthermore, TUNEL assay was conducted to determine the effects of diabetes on the cell survival of MSCs. Compared to the N-MSCs, D-MSCs showed significantly higher number of TUNEL positive cells. However, the percent of TUNEL positive cells in RD-MSCs was reduced to normal level (FIG. 4). These results suggest that apoptosis of MSCs observed in diabetes can also rescued by epigenetic compound treatment.

Figure 5:
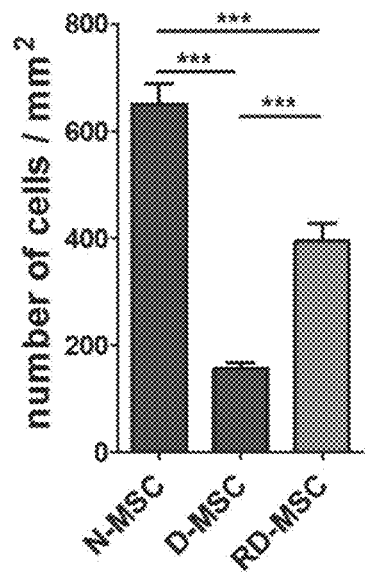
FIG. 5 shows data on the restoration of impaired adhesion of diabetic MSCs with compounds.
Figure 6:
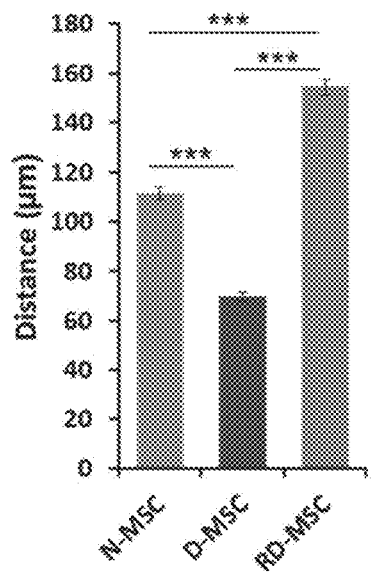
FIG. 6 shows data on the restoration of impaired cell movement of diabetic MSCs with compounds.
Figure 7:
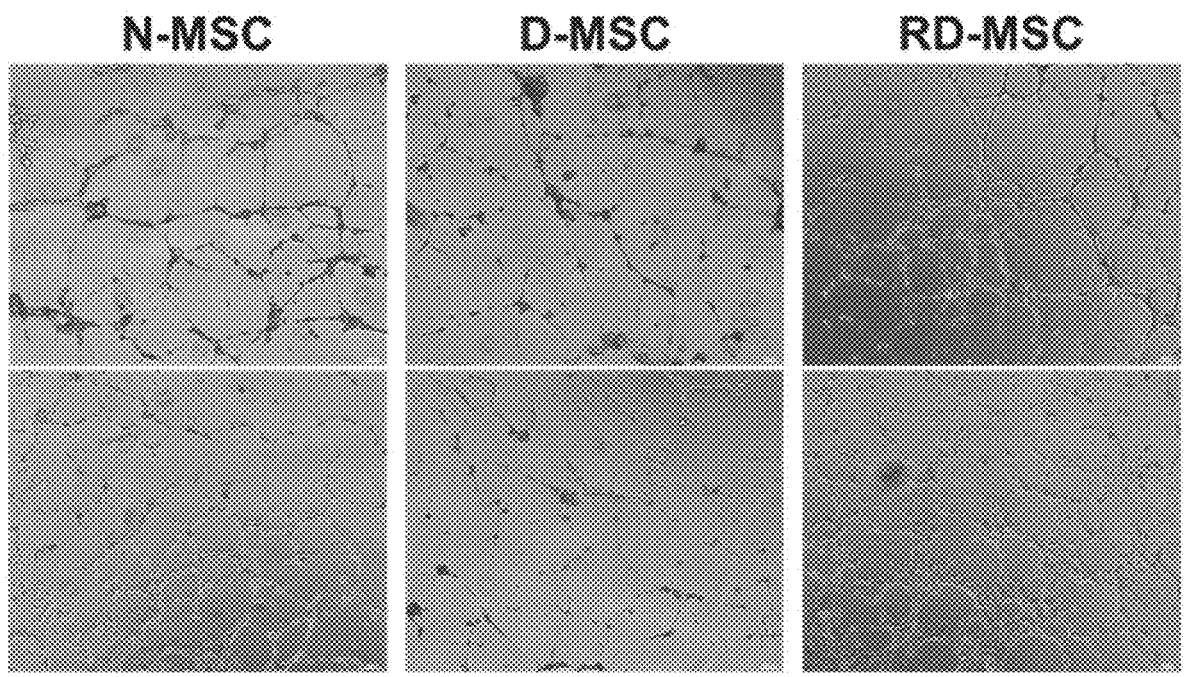
FIG. 7 shows data on the restoration of impaired tube formation of diabetic MSCs with compounds.

Restore of Impaired Angiogenic Cellular Functions of Diabetic MSCs with Compound To verify the angiogenic function in vitro, the adhesion capability of MSCs was compared because cell-adhesion mechanisms play a fundamental role during angiogenesis. Most of the adherent cells from normal bone marrow were spindle- or flatten-shaped, whereas the adherent cells from diabetes were rounded up showing that they are losing the adhesion capability. But the shape of adherent reprogrammed cells were similar to normal cells, and the number of adherent cells in these reprogrammed cells was also increased (FIG. 5). Also, wound healing assay to was performed verify the migration activity of different MSCs as the cellular function for angiogenesis. The distance of migrating D-MSCs was significantly decreased compared to N-MSCs, while RD-MSCs move faster than D-MSCs and even more than N-MSCs indicating that impaired cell migration of diabetic cells was restored (FIG. 6). Furthermore, the tube formation capability of each MSC were compared as an in vitro angiogenic index. HUVECs were plated onto Matrigel together with N-, D-, or RD-MSCs in the absence of additional angiogenic factors. The tubular structures were not clearly formed in the D-MSC group, but N- and RD-MSC group formed the similar tube-like structures suggesting that tube forming ability was also restored by compound treatment (FIG. 7). Taken together, these data indicated that epigenetic compounds increase the cellular function of D-MSCs for angiogenesis.

Reprogrammed D-MSC by Epigenetic Compounds Improved Hindlimb Ischemia In Vivo

Figure 8:
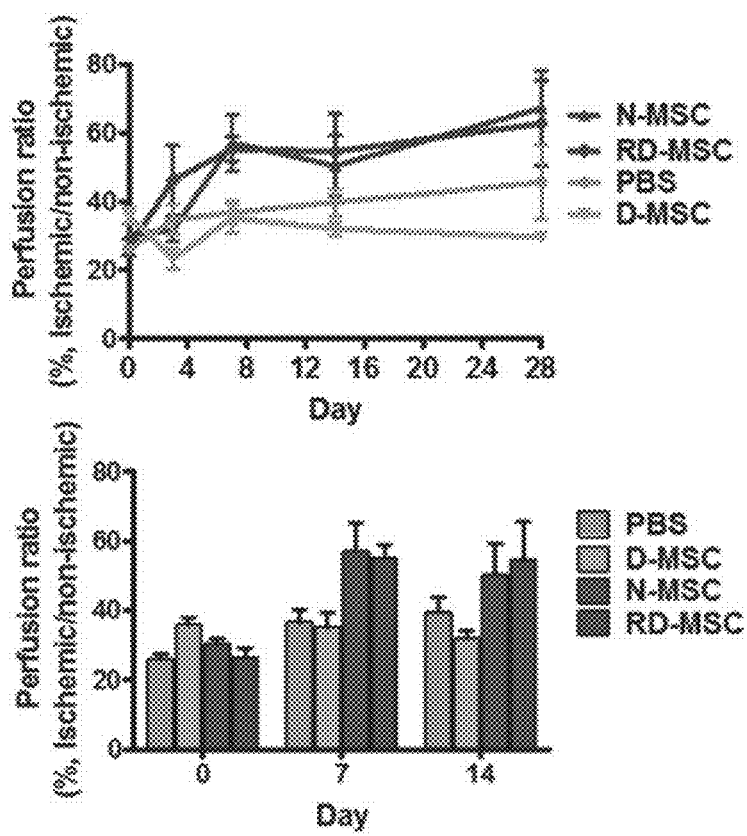
FIG. 8 shows data on the improvement of hindlimb ischemia by implantation of reprogrammed D-MSCs.
Figure 9:
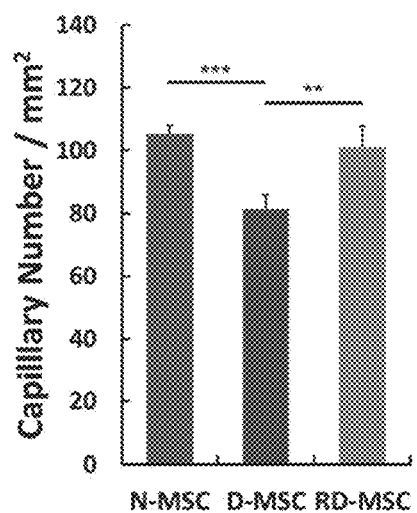
FIG. 9 shows data on the increased capillary density by implantation of reprogrammed D-MSCs.

To test the recovered therapeutic and regenerative effects of RD-MSCs, three hundred thousand N-, D-, or RD-MSCs were injected into ischemic hindlimbs and monitored blood flow using LDPI. PBS injection served as a control. Compared to the PBS-injected group, only the N- and RD-MSC implanted group showed significantly improved blood flow (FIG. 8), suggesting that the impaired regenerative capacity for limb ischemia of D-MSCs was restored by epigenetic compounds in experimental animal model. To further determine the neovascularization capability of reprogrammed D-MSCs, capillary density in the ischemic muscle was quantified after the cell implantation. Capillary density, determined by BSL-1 staining, was significantly different between the N-MSC and D-MSC implanted groups. RD-MSC injected group showed the significant increased number of capillary compared to D-MSC group (FIG. 9).

Restored Levels of Paracrine Factors in Ischemic Limbs Injected with RD-MSCs

Figure 10:
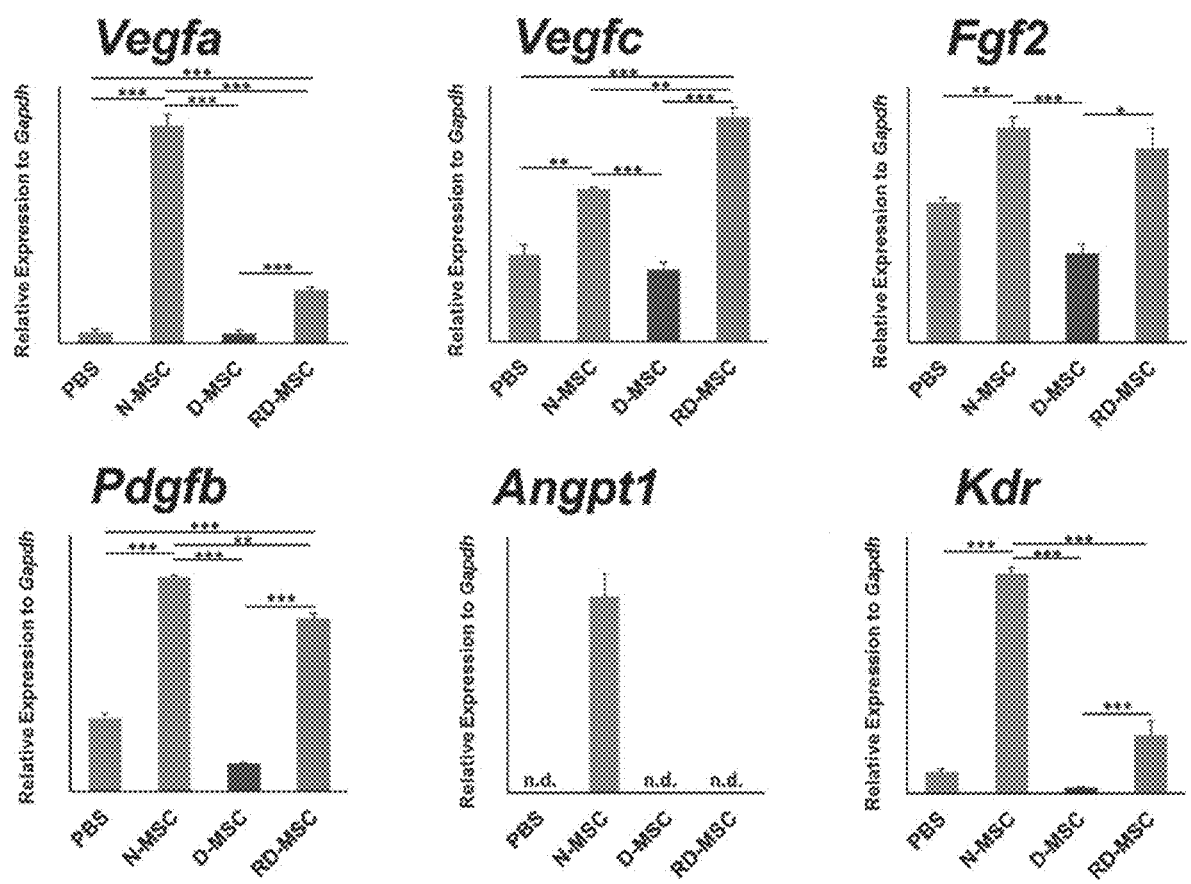
FIG. 10 shows data on the increased angiogenic factors by implantation of reprogrammed D-MSCs.

To investigate the changes of paracrine factors involved in neovascularization and apoptosis in vivo by the implantation of RD-MSCs, various gene expression levels were measured by real-time RT-PCR using muscles harvested at 2 weeks after cell implantation. The levels of Vegfa, Vegfc, Fgf2, Pdgfb, and Kdr were significantly increased in RD-MSC group compared D-MSC group which showed lower levels than in the N-MSC group (FIG. 10). However, Angp1 levels were not detected in RD-MSC group as well as D-MSC group. Together, these results suggest that the defective expression of angiogenic paracrine factors of D-MSCs is restored to higher levels of certain angiogenic factors up to N-MSCs by compound treatment.

Global Gene Expression Changes in Diabetic MSCs by Epigenetic Compounds

Figure 11:
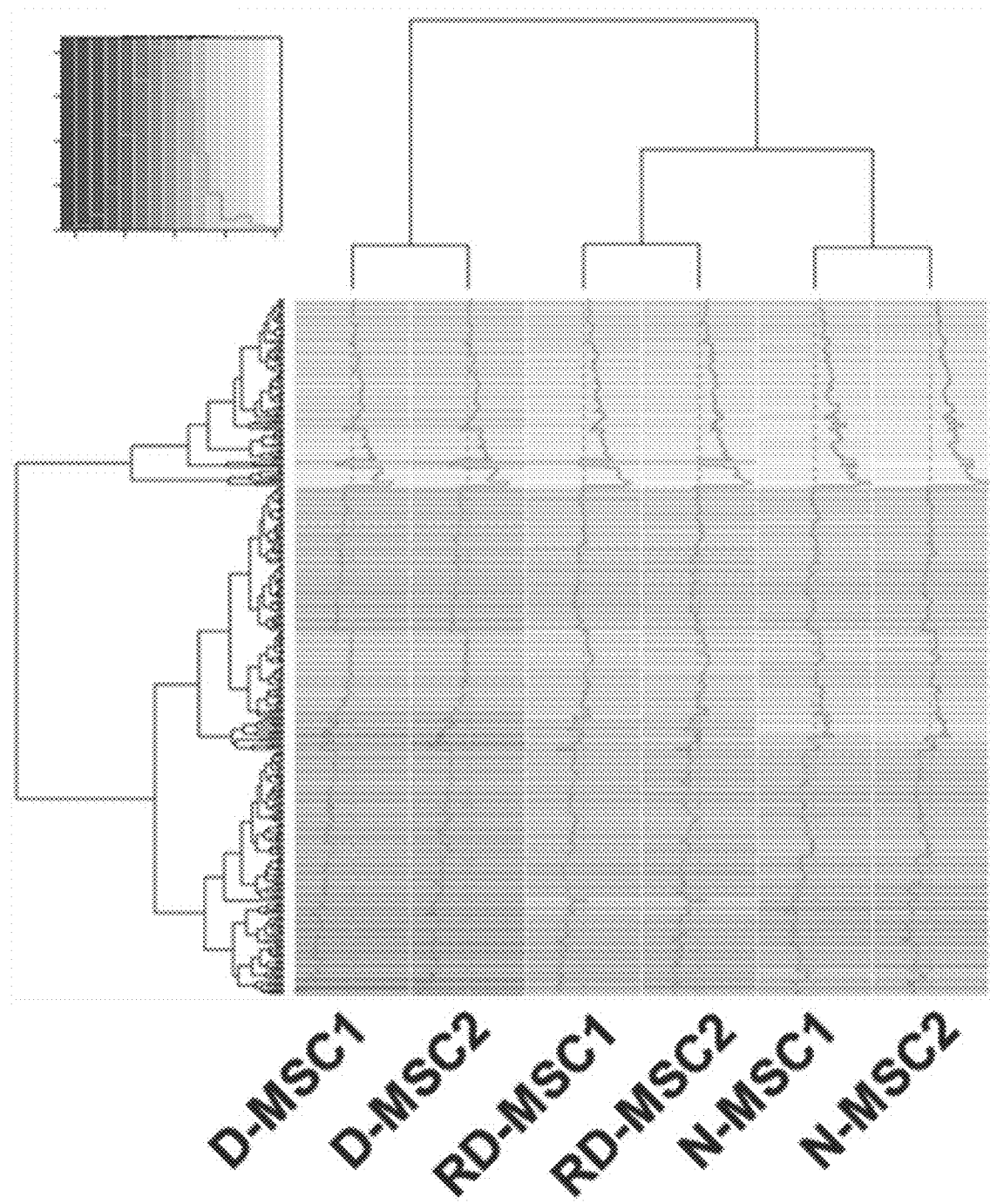
FIG. 11 shows data on the restoration of impaired global gene expressions in diabetic MSCs by epigenetic compounds. Heat map of differentially down-regulated genes in D-MSCs which were significantly increased in RD-MSC. The key represents FPKM normalized log 2 transformed counts.

To determine global gene expression changes in diabetic and epigenetic compound treating conditions in MSCs compared to normal conditions, the next-generation RNA-sequencing (RNA-seq) was performed with total RNAs from N-MSCs, D-MSCs, and RD-MSCs with two biological replicates. A total of 1,303 genes were identified were differentially and significantly down-regulated in D-MSCs compared to N-MSCs, and 350 genes out of these down-regulated subset of genes in D-MSC were significantly up-regulated by epigenetic compound in RD-MSC (FIG. 11). Down-regulated genes in D-MSCs compared to N-MSCs were enriched with functional annotation clusters associated with MAPK signaling pathway, mTOR signaling pathway, chemokine/cytokine signaling pathway, pathways in cancer, Jak-STAT signaling pathway, axon guidance as well as gene clusters involved in cellular carbohydrates metabolism including insulin signaling pathway. Notably, angiogenesis related gene groups such as gene clusters in VEGF signaling pathway, chemokine signaling pathway, and cell adhesion molecules; and immune response related gene clusters including leukocyte transendothelial migration, hematopoietic cell lineage, TB cell receptor signaling pathway, Fc epsilon RI signaling pathway, Toll-like receptor signaling pathway, NK cell mediated cytotoxicity, and complement/coagulation cascades were also repressed in diabetic cells.

Next, the effects of epigenetic compounds on diabetic-associated gene repressions was evaluated by comparing RNA-seq data from D-MSC and RD-MSC. Interestingly, only specific gene sets in D-MSC were restored by epigenetic compound although the target of this compound was known as general effector in epigenetic modulators. The most enriched down-regulating gene clusters in D-MSC such as MAPK signaling pathway, axon guidance, and VEGF signaling pathway, mTOR signaling pathway, and adipocytokine signaling pathway, as well as carbohydrate metabolisms were significantly increased in RD-MSC. However, immune response related gene sets were not restored by epigenetic compound except the genes in complementary/coagulation cascades Methods Isolation of Mesenchymal Stem Cells (MSCs) and Cell Culture.

Diabetes was induced in 8 week-old male Fischer 344 rats by intravenous injection of streptozotocin (5 mg/kg). Blood glucose levels were measured using an Accu-Check glucometer (Roche, Indianapolis, Ind.) after one week and two months. If blood glucose was higher than 200 mg/dl, rats were considered diabetic. Rats with glucose levels lower than 200 mg/dl were excluded from the study. Age- and sex-matched normal rats were used as controls. At 2 months after diabetes, bone marrow mononuclear cells were isolated using HISTOPAQUE®-1083 (Sigma-Aldrich, St. Louis, Mo.) according to the manufacturer's instructions. Whole bone marrow mononuclear cells from normal rats were plated in low glucose (100 mg/dl) Dulbecco's Modified Eagle Medium (DMEM, Invitrogen) supplemented with 15% FBS and antibiotics (Antibiotic-Antimycotic, Invitrogen). For diabetic MSCs, high glucose (450 mg/dl) DMEM supplemented with 15% FBS media was used. After 3 days of incubation in a humidified incubator at 37° C. with 5% $CO_2$, non-adherent hematopoietic cells were removed by changing media. The adherent MSCs were further cultured.

Passage two to four cells were used for study. At the 4 day of MSC culture, MSCs from diabetic rats were treated with various combinations of chemicals: 6 μM of SAHA, 1 μM of BIX01294, 2 μM of 5-aza (Dacogen), and 6 μM of CHIR99021 for 7 days.

Real-Time PCR

Gene expression was determined by TaqMan® real-time quantitative PCR on the 7300 Sequence Detection System (Applied Biosystems) using TaqMan® PCR Master Mix (Applied Biosystems). Total RNA was extracted from tissue or cells with RNeasy Plus Mini Kit (Qiagen, Carlsbad, Calif.) according to the manufacturer's instructions. First-strand cDNA was generated using the TaqMan® Multiscribe Reverse Transcription Kit (Applied Biosystems, Foster City, Calif.) primed with a mix of oligo dT and random hexamers. Relative mRNA expression of target gene normalized to GAPDH was calculated by using the formula Relative Expression Level=$2-\Delta Ct$, where $\Delta Ct=Ct$ gene of interest–Ct GAPDH. The primers and probes were designed using Primer Express 3.0 (Applied Biosystems).

MSC Proliferation and Colony Forming Unit Assay

For the cell proliferation assay, MSCs were plated at 200 cells/cm$^2$ and the number of resultant cells was determined. To evaluate proliferative cells, immunocytochemistry with anti-Ki-67 antibody (Millipore) was performed. For the colony forming unit assay, one hundred MSCs were plated onto 100 mm dishes and cultured for 14 days. The cells were stained with crystal violet and the number of colonies were counted.

Apoptosis Assay

In situ labeling of fragmented DNA was performed with terminal deoxynucleotidyltransferase (TdT)-mediated dUTP-biotin nick end labeling (TUNEL) method with the use of an in situ cell detection kit (Roche) as previously described.

Cell Adhesion Assay

Ninety-six well plates were pre-coated with 1 μg/well vitronectin (Sigma), 10 μg/well collagen (Sigma, MO), 10 μg/well laminin (BD Biosciences), and 20 μg/well fibronectin (Sigma) respectively at 4° C. overnight. Plates were washed with PBS and incubated for 1 hour with 1% bovine serum albumin to block remaining protein binding sites. 2.5×10$^4$ of bone marrow-derived rat mesenchymal stem cells; N-MSC, D-MSC, and RD-MSC, were seeded on 96 well plates and cultured in DMEM medium for 24 hour at 37° C. and 5% CO2. Cells were gently washed three-times with PBS and adherent cells were counted under phase contrast microscopy (Nikon Eclipse Ti).

Wound Healing Assay

MSCs were plated in confluence in 24-well plates (1.5× 10$^5$ cells/300 μl/well) and starved for 24 h in serum-free DMEM media. After 24 h the medium was discarded and the monolayer was scratched with a sterile plastic pipette tip. The cells were washed three times with DMEM, and 300 μl of DMEM medium with serum were added. At 0 and 24 h, images were taken (Nikon Eclipse Ti). The area of each dish was measured using Image J.

Tube Formation Assay

Glass chamber slides were coated with Matrigel (Becton Dickinson) and overlaid with 7×10$^4$ human umbilical vein endothelial cells together with 2.5×10$^5$ MSCs in endothelial basal medium (EBM, Cambrex Bio Science) in the absence of additional growth factors or cytokines and incubated at 37° C., 5% CO$_2$ for 16 hours. The tube formation was evaluated using a phase-contrast microscope.

In Vivo Hindlimb Ischemia Experiments

Unilateral hindlimb ischemia was created in normal F344 rats by ligation of the femoral artery and removing all arterial branches. Three hundred thousand DiI-labeled MSCs in 500 μl of PBS were intramuscularly injected into the ischemic hindlimbs. Blood flow in the hindlimb was measured using a Laser Doppler perfusion imager (LDPI, Moor instrument, UK). Mean values of perfusion was calculated from the stored digital color-coded images. The level of blood flow of the ischemic (left) limb was normalized to that of non-ischemic (right) limb to avoid data variations caused by ambient light and temperature. Four weeks after the injection of N-, D-, or RD-MSCs into ischemic hindlimbs, the hindlimb muscles were harvested, fixed with 4% paraformaldehyde at 4° C. overnight, and frozen-sectioned. To visualize capillaries, the sections were stained using BS lectin-I and the capillary density was determined under conventional epifluorescence microscopy.

Next-Generation RNA Sequencing

The converted cDNAs from isolated RNAs, immunoprecipitated/captured DNA, input, and negative control (in the absence of biotin) were used to generate DNA libraries following the Illumina protocol. 38-cycle single end sequencing was performed. Image processing and sequence extraction were done using the standard Illumina Pipeline. Two independent libraries and runs (one lane per library) for each biological replicate were generated. FASTQ sequence files were aligned to reference genome using Bowtie. The best alignment and reporting option were used for all conditions, corresponding to no more than 2 bp mismatches across each 38 bp read. Mapped reads were assembled into RNA transcripts using the Cufflinks software (version 1.3.0). Cufflinks was run using the annotation file of known genes and the mapped reads produced by Tophat. Fragments Per Kilobase of exon model per Million mapped fragments (FPKM) value (a normalized gene expression value that are comparable between different samples and genes) together with confidence intervals were estimated for each replicate. R/bioconductor packages were used to generate the heatmap and box plot of the different expressed genes comparing N-MSC, D-MSC, and RD-MSC. Database for Annotation, Visualization and Integrated Discovery (DAVID) tool was used to generate the functional annotation charts for impaired (N-MSC vs. D-MSC) and restored (D-MSC vs. RD-MSC) gene expressions.

ChIP-PCR

The cells were grown on the 10-cm plates to 85% confluence. Formaldehyde was added to a final concentration of 1%, and the plates were incubated for 10 min at 37° C. The cross-linking reaction was stopped by the addition of 100 mM glycine containing protease inhibitors (Complete; RocheApplied Science). Cells were washed in dilution buffer (0.01% SDS, 1% Triton X-100, 1.2 mM EDTA, 16.7 mMTris-HCl, 150 mMNaCl, pH 8.0 plus protease inhibitors), resuspended in lysis buffer (1% SDS, 10 mM EDTA, 50 mMTris-HCl, pH 8.0 plus protease inhibitors) and sonicated to shear the DNA into 0.3~3-kb fragments. Following sonication and centrifugation, sheared chromatin was incubated with anti-H3K9/14 antibodies, that can detect the changes of histone acetylation as activation mark, or anti-rabbit IgG antibody (negative control) overnight at 4° C. Then, protein G beads were added and the chromatin was incubated for 2 hours in rotation. An aliquot of chromatin that was not incubated with an antibody was used as the input control sample. Antibody-bound protein/DNA complexes were eluted and subjected to PCR analysis.

Synthesis of Quinazoline Derivatives

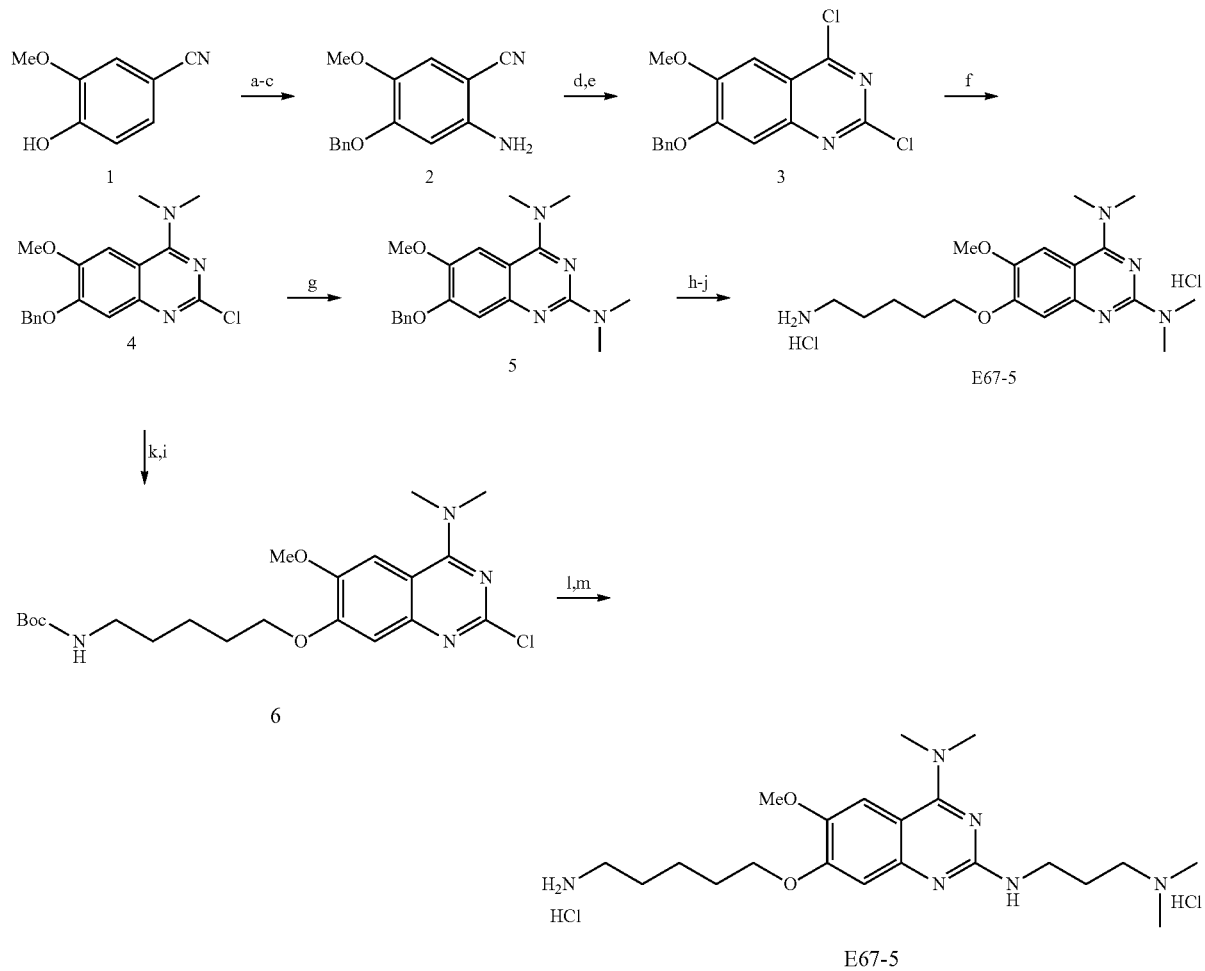

Reagents and conditions: (a) Benzyl bromide, K$_2$CO$_3$, dry DMF, rt; (b) HNO$_3$ 69.5%, (Ac)$_2$O, 0° C. then rt, (c) iron dust, NH$_4$Cl, i-PrOH-H$_2$O (5:3), reflux; (d) i) methyl chloroformate, DIPEA, DMF-DCM (2:1), 0° C. then rt, ii) H$_2$O$_2$ 30%, NaOH, EtOH; (e) POCl$_3$, N,N-diethylaniline, reflux; (f) dimethylamine 2M in THF, dry THF, rt; (g) dimethylamine 2M in THF, dry THF, 110° C., sealed tube; (h) H$_2$, Pd-C, dry THF-MeOH (2:1), 1 atm, rt; (i) tert-butyl (5-hydroxypentyl)carbamate, PPh$_3$, DIAD, dry THF, N$_2$, rt; (j) HCl 4N in dioxane, dry THF, rt; (k) TFA, reflux; (l) N$^1$,N$^1$-dimethylpropane-1,3-diamine, 110° C., sealed tube; (m) HCl 4N in dioxane, dry THF-MeOH (1:1), rt.

7-((5-aminopentyl)oxy)-N$^2$-(3-(dimethylamino)propyl)-6-methoxy-N$^4$,N$^4$-dimethylquinazoline-2,4-diamine (E67-2): $^1$H-NMR (400 MHz, DMSO) δ 1.50 (m, 2H, CH$_2$CH$_2$CH$_2$O), 1.65 (m, 2H, CH$_2$CH$_2$CH$_2$CH$_2$O), 1.81 (m, 2H, CH$_2$CH$_2$O), 2.80 (m, 2H, H3N$^+$CH$_2$CH$_2$), 3.26 (s, 6H, N(CH$_3$)$_2$), 3.45 (s, 6H, N(CH$_3$)$_2$), 3.87 (s, 3H, OCH$_3$), 4.08 (m, 2H, CH$_2$CH$_2$CH$_2$O), 7.45 (s, 1H, H quinazoline ring), 7.76 (s, 1H, H quinazoline ring), 7.99 (s br, 3H, H$_3$N$^+$), 12.1 (s br, 1H, HN$^+$ quinazoline ring).

7-((5-aminopentyl)oxy)-6-methoxy-N$^2$,N$^2$,N$^4$,N$^4$-tetramethylquinazoline-2,4-diamine (E67-5): $^1$H-NMR (400 MHz, DMSO) δ 1.50 (m, 2H, CH$_2$CH$_2$CH$_2$O), 1.64 (m, 2H, CH$_2$CH$_2$CH$_2$CH$_2$O), 1.81 (m, 2H, CH$_2$CH$_2$O), 1.99 (m, 2H, NHCH$_2$CH$_2$), 2.74 (s, 6H, $^+$HN(CH$_3$)$_2$), 2.80 (m, 2H, H3N$^+$CH$_2$CH$_2$), 3.11 (m, 2H, CH$_2$CH$_2$N(CH$_3$)$_2$H$^+$), 3.47 (s, 6H, N(CH$_3$)$_2$), 3.49 (m, 2H, NHCH$_2$CH$_2$CH$_2$), 3.86 (s, 3H, OCH$_3$), 4.09 (m, 2H, CH$_2$CH$_2$CH$_2$O), 7.15 (s, br, 1H NHCH$_2$CH$_2$CH$_2$), 7.45 (s, 1H, H quinazoline ring), 7.93 (m, 4H, H quinazoline ring and H$_3$N$^+$), 10.6 (s, br, $^+$HN(CH$_3$)$_2$), 12.8 (s br, 1H, HN$^+$ quinazoline ring).

Additional compounds below were prepared by using the same or similar conditions by substituting appropriate starting materials.

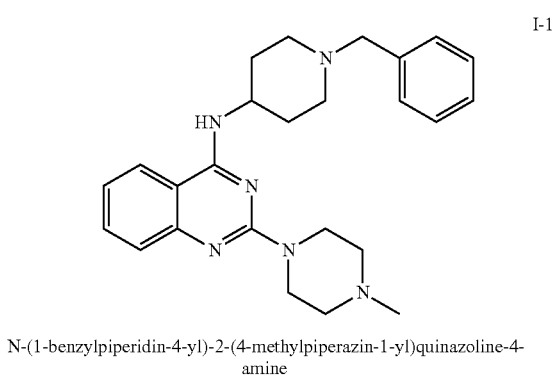

N-(1-benzylpiperidin-4-yl)-2-(4-methylpiperazin-1-yl)quinazoline-4-amine

I-1

-continued

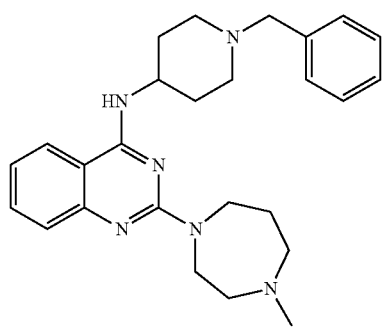

N-(1-benzylpiperidin-4-yl)-2-(4-methyl-1,4-diazepan-1-yl)quinazolin-4-amine

I-2

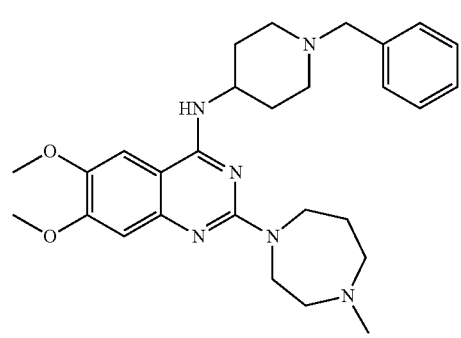

N-(1-benzylpiperidin-4-yl)-6,7-dimethoxy-2-(4-methyl-1,4-diazepan-1-yl)quinazolin-4-amine (BIX-01294)

I-3

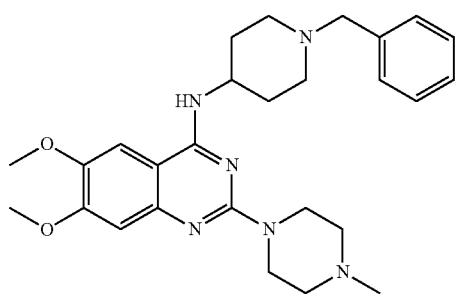

N-(1-benzylpiperidin-4-yl)-6,7-dimethoxy-2-(4-methylpiperazin-1-yl)quinazolin-4-amine

I-4

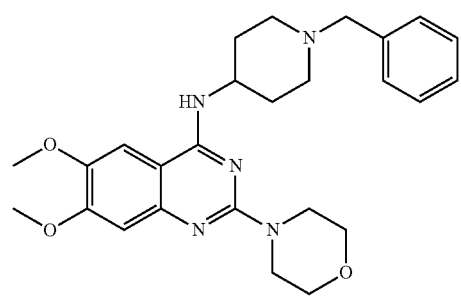

N-(1-benzylpiperidin-4-yl)-6,7-dimethoxy-2-morpholinoquinazolin-4-amine

I-5

-continued

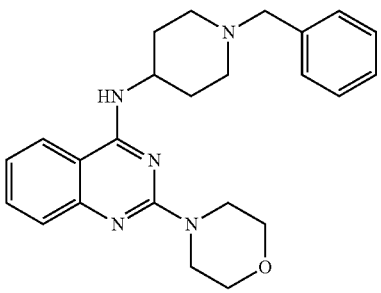

N-(1-benzylpiperidin-4-yl)-2-morpholinoquinazolin-4-amine

I-6

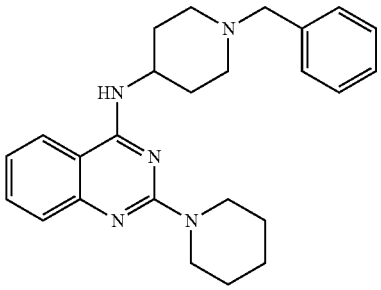

N-(1-benzylpiperidin-4-yl)-2-thiomorpholinoquinazolin-4-amine

I-7

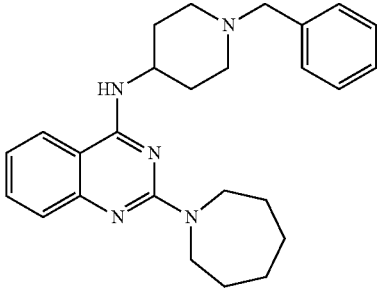

N-(1-benzylpiperidin-4-yl)-2-(piperidin-1-yl)quinazolin-4-amine

I-8

2-(azepan-1-yl)-N-(1-benzylpiperidin-4-yl)quinazolin-4-amine

I-9

I-10

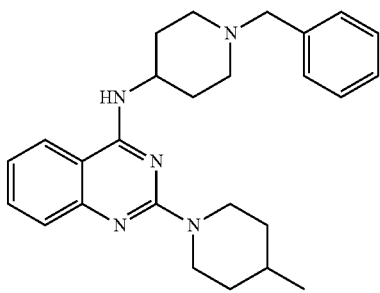

N-(1-benzylpiperidin-4-yl)-2-(4-methylpiperidin-1-yl)quinazolin-4-amine

I-11

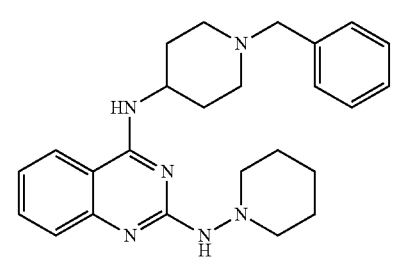

$N^4$-(1-benzylpiperidin-4-yl)-$N^2$-(piperidin-1-yl)quinazoline-2,4-diamine

I-12

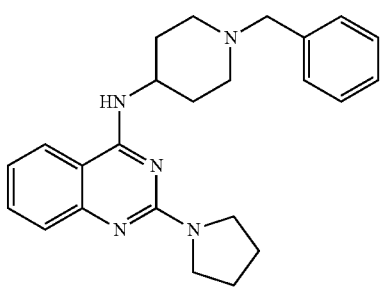

N-(1-benzylpiperidin-4-yl)-2-(pyrrolidin-1-yl)quinazolin-4-amine

I-13

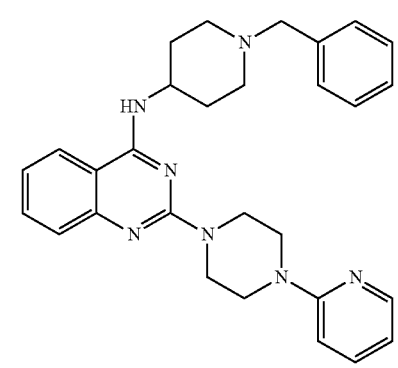

N-(1-benzylpiperidin-4-yl)-2-(4-(pyridin-2-yl)piperazin-1-yl)quinazolin-4-amine

I-14

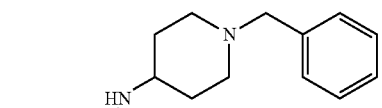

(4-(4-((1-benzylpiperidin-4-yl)amino)quinazolin-2-yl)piperazin-1-yl)(phenyl)methanone

I-15

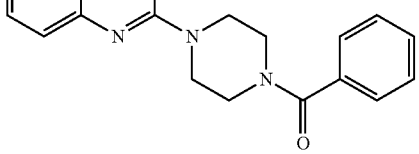

$N^4$-(benzylpiperidin-4-yl)-$N^2$-(3(dimethylamino)propyl)quinazoline-2,4-diamine

I-16

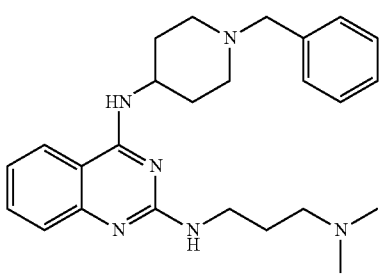

$N^4$-(1-benzylpiperidin-4-yl)-$N^2$-(2-dimethylamino)ethyl)quinazoline-2,4-diamine

I-17

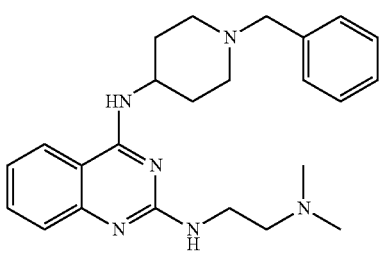

2-((4-((1-benzylpiperidin-4-yl)amino)quinazolin-2-yl)amino)ethanol

I-18

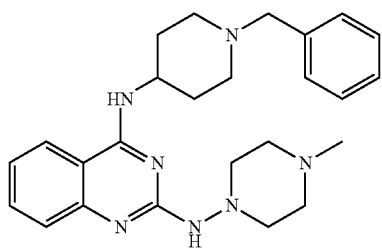

N⁴-(1-benzylpiperidin-4-yl)-N²-(4-methylpiperazin-1-yl)quinazoline-2,4-diamine

I-19

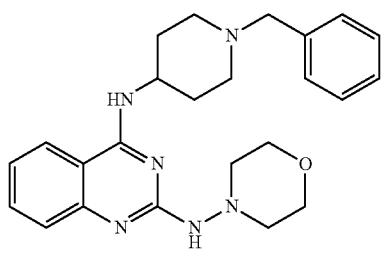

N⁴-(1-benzylpiperidin-4-yl)-N²-morpholinoquinazoline-2,4-diamine

I-20

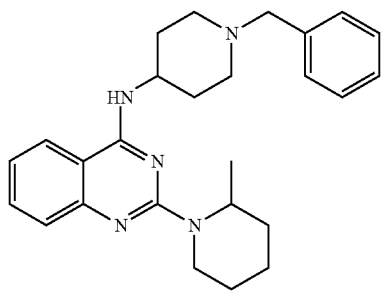

N-(1-benzylpiperidin-4-yl)-2-(2-methylpiperidin-1-yl)quinazolin-4-amine

I-21

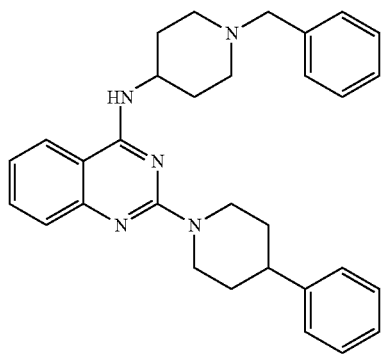

N-(1benzylpiperidin-4-yl)-2-(4-phenylpiperazin-1-yl)quinazolin-4-amine

E72

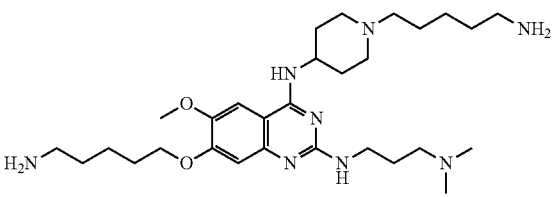

7-((5-aminopentyl)oxy)-N⁴-(1-5-aminopentl)piperidin-4-yl)-N²-(3-(dimethylamino)propyl)-6-methoxyquinazoline-2,4-diamine Gene Expression Pattern and DNA Methylation at the Promoter Regions of Angiogenic Genes in Endothelial Progenitor Cells (EPCs)

To prepare diabetic endothelial progenitor cells (EPCs) D-EPCs, streptozotocin (STZ)- was used to induce diabetes in rats (12 wks after the onset of diabetes). For normal EPCs (N-EPCs), age- and sex-matched non-diabetic (normal) rats were used. To culture EPCs, bone marrow (BM)-derived mononuclear cells (MNCs) isolated from the tibia and femur were plated on cell culture dishes coated with rat vitronectin and cultured in EBM-2 medium containing 5% FBS and cytokine cocktail, singleQuots® for 7 days. differential expression of angiogenic genes between N-EPCs and DEPCs were investigated by using an Angiogenesis Microarray kit (Oligo GEArray® kit, Superarray bioscience) (FIG. 12). The left panel shows a set of representative mRNA expression profiles comparing N-EPCs and D-EPCs. The microarray profiles illustrate some of the increased (>5 fold) angiogenic factors (the black spots) in N-EPCs v.s., D-EPCs. Gene expression is significantly suppressed in D-EPCs.

To test the reversible changes of gene expression and DNA methylation of such gene promoters in D-EPCs by compound epigenetic regulators, epigenetic profiling studies on D-EPCs were performed. STZ-induced diabetic rats 12 wks after the onset of diabetes were used. Age- and sex-matched rats were used as non-diabetic controls. At the 4 day of EPC culture, EPCs from diabetic rats were treated with various combinations of chemicals: 0.5 mM of BIX-01294, 1 mM of VPA, and 5~M RG108. Cells were collected at the 10 day of culture for extraction of genomic DNAs and RNAs for epigenetic profiling by modified methylation-sensitive restriction enzyme (MSRE)-PCR assay (EpiMark™, NEB) and qRT-PCR, respectively.

For MSRE-PCR assay, purified genomic DNAs were treated with methylation sensitive restriction enzyme, followed by the treatment of T4-BGT and UDP-Glucose (UDP-Glc) for adding a glucose moiety to 5-hydroxymethylcytosine (5-hmC). Real time PCR of the experimental (glucosylated) and control (mock glucosylated) target DNA with specific primers flanking a CCGG site of interest was performed to measure the amount of DNA methylation at specific promoter region of target genes.

Figure 13:
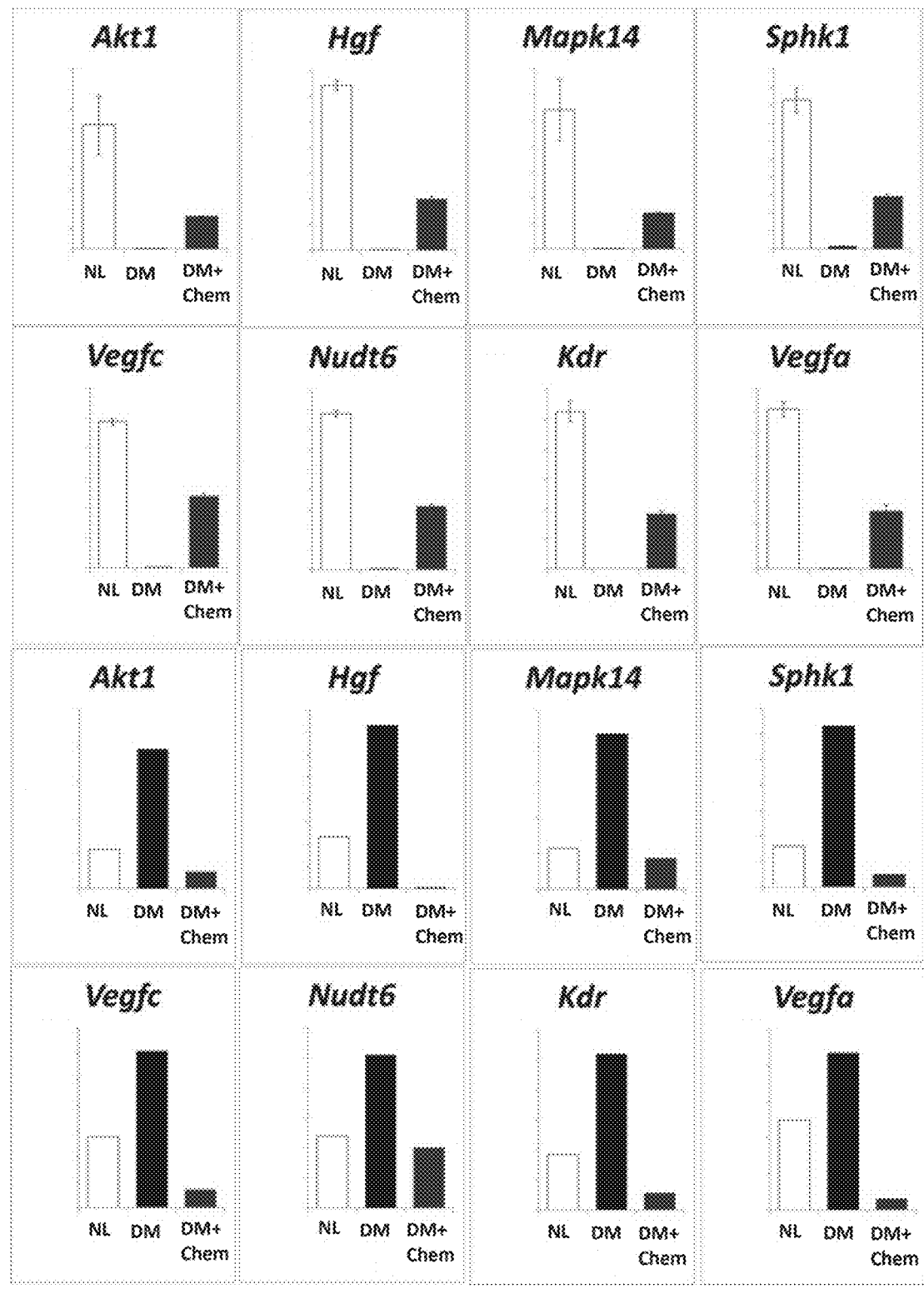
FIG. 13 shows gene expression patterns (top) and DNA methylation (bottom) at the promoter regions of angiogenic genes in EPCs.

The results of MSRE-PCR showed that D-EPCs have significantly high DNA methylation in the promoters of angiogenic genes such as Akt1, Hgf, Mapk14, Sphk1, Vegfc, Nudt6, Kdr, Vegfa, and Pten which were identified by the above microarray studies, and treatments with compounds reduced DNA methylation at these promoters and enhance gene expression (FIG. 13). In addition, reduced cell biologic function such as cell adhesion, migration and tube formation were all increased.

Human BM-derived EPCs were cultured similarly. Two approaches were used for reprogramming diabetic EPCs. Initially we used an unselected approach employing combinations of compounds. For the combinatorial approach, combinations of the three classes of compounds were used and the gene and epigenetic changes were determined. In the next targeted approach, selective reagents were chose accordingly to the methylation and histone modification status of key factors identified.

Studies indicate that EPC function may be attributed to VEGF, SDF-1, CXCR4, HIF1α, IGF-1, or Akt12.

EPCs from diabetic subjects were cultured. The cultured EPCs are typically reseeded at day 4 and cultured for another 3-7 days. HDAC inhibitors—SAHA, sodium butyrate, and VPA, two DNA methylation inhibitor 5-Aza and RG108, and multiple histone 3 lysine 9 (H3K9) methyltransferases G9a and GLP inhibitors of formula I were used. Compounds were tested to find candidates which induce the highest cell functionality with minimum toxicity. The following assays was conducted comparing N-EPCs, D-EPCs, and rescued diabetic EPCs (RD-EPCs) to determine rescued diabetic (RD)-EPCs with respect to their biological potency. Cell biological assays (adhesion, migration, proliferation and tube formation) were performed as well as angiogenic and neurotrophic gene assays (low density qRT-PCR array). In some samples, western blot (WB) or ELISA was performed to confirm results. In vivo vessel forming capability were tested by Matrigel plug, corneal micropocket, and ear or skin wound assays.

RD-EPCs were identified that possess the highest angiogenic and neurotrophic capacity. In this EPC reprogramming, a short duration of compound treatment should be sufficient to reverse the epigenetic modifications incurred by diabetes, and culture conditions will then guide their fate back to more naïve EPCs. This new reprogramming technology can be applied and expanded to diabetic bone marrow-derived stem or progenitor cells including MSCs, EPCs, and even to unfractionated bone marrow-derived mononuclear cells (BM-MNCs).

What is claimed:

1. A method of treating or preventing a diabetic disease or condition comprising:
   mixing progenitor cells from a human subject diagnosed with diabetes and a composition comprising a histone deacetylase inhibitor under conditions such that epigenetically modified cells with enhanced angiogenic gene expression are produced;
   administering an effective amount of a composition comprising the epigenetically modified cells or cells cultured therefrom to a subject in need thereof, and wherein the progenitor cells were obtained from the subject receiving the administered composition.

2. The method of claim 1, wherein the progenitor cells are bone marrow derived cells, endothelial progenitor cells, or mesenchymal stem cells.

3. The method of claim 1, wherein the diabetic disease or condition is diabetic wounds or diabetic neuropathy.

4. The method of claim 1, wherein the histone deacetylase inhibitor is suberoylanilide hydroxamic acid or salt thereof.

5. The method of claim 1, wherein the diabetic disease or condition is peripheral vascular disease, cardiovascular disease, or stroke.

* * * * *